United States Patent [19]

Nicholson

[11] Patent Number: 4,584,530

[45] Date of Patent: Apr. 22, 1986

[54] ELECTROLYTE POTENTIAL MEASURING APPARATUS

[76] Inventor: John P. Nicholson, R.R. 5, Orangeville, Canada, L9W 2Z2

[21] Appl. No.: 494,068

[22] Filed: May 12, 1983

[30] Foreign Application Priority Data

Feb. 28, 1983 [CA] Canada .................................. 422490

[51] Int. Cl.⁴ ........................................... G01N 27/42
[52] U.S. Cl. ................................... 324/425; 324/71.1; 324/72; 324/450; 324/347; 324/348; 324/207
[58] Field of Search ................... 324/65 LR, 65 P, 72, 324/72.5, 174, 251, 347, 348, 363, 444, 445, 446, 447, 449, 220, 207, 71.1, 425, 439, 450

[56] References Cited

U.S. PATENT DOCUMENTS

| | | | |
|---|---|---|---|
| 1,163,469 | 12/1915 | Schlumberger . | |
| 2,105,247 | 1/1938 | Jakosky | 175/182 |
| 2,192,404 | 3/1940 | Jakosky | 175/182 |
| 2,256,742 | 9/1961 | Jakosky | 175/182 |
| 2,948,852 | 8/1960 | Bacon | 324/174 |
| 2,974,276 | 3/1961 | Davis | 324/444 |
| 3,496,457 | 2/1970 | Proctor et al. | 324/220 |
| 3,735,249 | 5/1973 | Stoll | 324/348 |
| 4,151,458 | 3/1979 | Seager | 324/9 |
| 4,197,176 | 4/1980 | Ensanian | 324/71.1 |
| 4,228,399 | 10/1980 | Rizzo et al. | 324/425 |
| 4,322,805 | 3/1982 | Rog et al. | 364/481 |
| 4,356,444 | 10/1982 | Saenz, Jr. | 324/54 |
| 4,365,191 | 12/1982 | Weldon et al. | 324/71 R |
| 4,388,594 | 6/1983 | Deskins et al. | 324/348 |
| 4,414,511 | 11/1983 | Waits et al. | 324/347 |
| 4,438,391 | 3/1984 | Rog et al. | 324/71.1 |

OTHER PUBLICATIONS

Materials Protection and Performance-vol. 12, Oct. 1973, No. 10-"Continuous Recording of Surface Potentials vs. Distance"-Robert L. Davis, pp. 49-59.

Primary Examiner—Reinhard J. Eisenzopf
Assistant Examiner—Kevin D. O'Shea
Attorney, Agent, or Firm—Burgess, Ryan & Wayne

[57] ABSTRACT

The present invention relates to a wheel electrode suitable for use with a device for making an electrical survey of a structure contained in an electrolyte. The wheel electrode includes a chamber which contains electrolytic solution and a porous rim. The rim includes a dielectric rim structure having at least one recess in its axial surface, a plurality of apertures passing through the rim structure into the recess, and at least one porous member securable in the recess and having a predetermined rate of permeation. A metal electrode is positioned in the chamber in contact with the electrolytic solution. An elastic porous rim cover is securable about the rim for making contact with the electrolyte. The rim cover is adapted to carry an electrically conductive solution to the electrolyte during wheel rotation. Generating mechanisms are spaced about the wheel electrode at predetermined intervals for generating a series of electrical signals as the wheel electrode rotates. A count of these signals is indicative of the distance travelled by the wheel electrode.

8 Claims, 7 Drawing Figures

ELECTROLYTE POTENTIAL MEASURING APPARATUS

The present invention relates to a device for making an electrical survey of a structure contained in electrolyte. In particular, the present invention relates to a wheel electrode rotatably mounted to the surveying device.

A potential survey of the reinforced steel concrete structure is commonly made to detect the amount of corrosion that has occurred in a structure. Usually these surveys are conducted by taking measurements of voltage potentials at predetermined locations along a relatively flat surface of the reinforced concrete structure. These readings or measurements will commonly be made at a 3 to 5 foot or larger grid distance separation and are manually transferred to a graphic representation of the structure. These measurements are made by manually placing a copper-copper-sulphate electrode on the surface of the concrete and recording the voltage potential displayed on a voltmeter or potentiometer connected to the electrode.

As can be appreciated, when large surfaces are to be surveyed, this manual survey can be expensive in terms of labor cost.

U.S. Pat. No. 2,974,276 issued Mar. 7, 1961 to R. L. Davis teaches a wheel electrode which is able to reduce the time involved for surveying earth potentials; however, the Davis wheel electrode is not applicable for use in concrete structures. The Davis wheel electrode comprises a pair of dielectric disks securable at their peripheries to a porous dielectric rim. A chamber is defined between the disks for containing electrolytic solution. A metal electrode is suspended from the axle of the wheel electrode. The metal electrode is maintained in electrical contact with the rim through the electrolytic solution. The Davis reference teaches recording the voltage measurements on a continual basis by use of a stylus which moves at a speed proportional to the movement of the wheel electrode. Davis teaches connecting a speedometer cable directly to the wheel electrode.

One disadvantage with the Davis wheel electrode is that in order to provide good electrical contact with the rim, Davis teaches digging a trench in the earth and filling it with an electrolytic solution. This step is costly in terms of labor and is impractical for applications with respect to reinforced concrete, or other electrolytes that cannot be excavated and filled with an electrolytic solution. The impracticallity of using the Davis wheel electrode on concrete is evidenced in FIG. 7 of the Davis patent wherein readings for the road and concrete show downwardly extending spikes.

Still yet another disadvantage with the teachings of the Davis patent is the fact that the connection of a speedometer cable to the wheel electrode is cumbersome because gearing is required proximate the wheel for effecting rotation of the cable. Further, this gearing may become clogged with dirt when used in the field resulting in faulty distance measurement.

The impracticality of using a speedometer cable attached to the Davis wheel electrode is further evidenced in an article given by R. L. Davis in the Materials Protection And Performance magazine, Vol. 12, No. 10, pages 49 to 59 (1973) (October). At page 53 and 55 of this article, Davis teaches driving his chart recorder at a speed proportionate to the speed at which the wire extending between the surveying device and a reference point is expired.

U.S. Pat. No. 4,322,805 issued to Rog et al teaches an electrical survey method and apparatus wherein the recording of information is done at predetermined spaced intervals along the length of the survey. This is accomplished by using magnets in a Hall effect transistor to generate a series of electrical signals indicative of the length of cable expired during the survey.

The disadvantage with measuring the length of cable expired is that this type of measurement promotes inaccuracies in distance travelled by the electrode and, accordingly, the position of where the measurement has been taken. These inaccuracies are due to slack or snags in the wire along the earth on which the wire lies or other obstructions over which the wire must pass. Further, the procedure of measuring the length of the wire expired from a reference point is not well suited for measurements to be taken at grid matrix locations with respect to the reference point.

It is therefore an object of the present invention to provide a wheel electrode suitable for use with a device for making an electrical survey of a structure contained in electrolyte wherein the permeation of electrolyte through the wheel electrode is controlled.

It is another object of the present invention to provide a wheel electrode suitable for use with a device for making an electrical survey of a structure contained in electrolyte wherein the coordinates for the measured potential are measured directly from the wheel electrode.

It is another object of the present invention to provide a wheel electrode suitable for use with a device for making an electrical survey of a structure contained in electrolyte wherein no pretreatment of the electrolyte is required.

In accordance with one aspect of the present invention there is provided a wheel electrode suitable for use with a device for making an electrical survey of a structure contained in electrolyte. The wheel electrode comprises a porous rim means, a chamber, metal electrode means, and elastic porous rim cover means. The rim means is permeable with electrolytic solution to permit conduction therethrough. The chamber contains the electrolytic solution which communicates with the porous means. The metal electrode means is in the chamber in contact with the electrolytic solution for the purpose of sensing electrolytic voltage potentials in the electrolyte. The rim cover means is securable about the rim means for contacting the electrolyte. The rim cover means is adapted to carry an electrically conductive solution to the electrolyte as the rim cover means makes contact with the electrolyte. By providing an elastic porous rim cover means the present invention provides a wheel electrode which makes continuous contact with the electrolyte and accommodates for irregularities in the electrolyte surfaceby temporarily deformation of the rim cover means. Further, by transmitting the electrically conductive solution to the electrolyte the electrical contact between the wheel electrode and the electrolyte is enhanced.

In accordance with another aspect of the present invention there is provided a wheel electrode suitable for use with a device for making electrical surveys of structures contained in electrolyte. The wheel electrode comprises a porous rim means, a chamber, and metal electrode means. The porous rim means includes a dielectric rim structure having at least one recess in its axial surface and a plurality of apertures passing through the rim structure into the recess. The dielectric rim further includes one or more porous members securable in the recess and having a predetermined rate of permeation whereby the electrolytic solution provides a continuous conducting path. The chamber contains the electrolytic solution which communicates with the porous rim means. The metal electrode means is in the chamber in contact with the electrolytic solution for sensing electrolytic voltage potentials in the electrolyte.

Additionally, the wheel electrode may include a plurality of recesses spaced apart at predetermined intervals with at least one of the apertures being located below each of the recesses, and one of the porous members located in each recess. It is further envisaged that the porous members may comprise a ceramic material such as for example, sintered aluminum oxide. The predetermined intervals may be chosen to maintain ionic conduction between the electrolyte and metal electrode. The porous members having the predetermined rate of permeation slows the flow rate at which electrolytic solution flows out of the chamber. As a result, the use of electrolytic solution is controlled.

In accordance with another aspect of the present invention there is provided a wheel electrode suitable for use with a device for making an electrical survey of a structure contained in electrolyte. The wheel electrode comprises a porous rim means permeable with electrolytic solution to permit conduction therethrough. The wheel electrode further comprises a chamber for containing the electrolytic solution which communicates with the porous rim means. The wheel electrode includes metal electrode means in the chamber in contact with the electrolytic solution for sensing electrolytic voltage potentials in the electrolyte. In this aspect of the present invention a generating means is provided spaced about the wheel electrode at predetermined intervals for generating a series of electrical signals as the wheel electrode rotates whereby a count of the signals is indicative of the distance travelled by the wheel electrode over the electrolyte.

It is further envisaged that the device may include a sensing means responsive to the passing of the generating means to thereby generate the electrical signals. By providing a mechanism which generates electrical signals from the wheel electrode which are representative of the distance travelled by the wheel electrode, a more accurate representation of the distance travelled by the wheel electrode is given because the generation of electrical signals is not effected by buildup of dirt and the like on the wheel. Also, by placing the generating means on the wheel electrode measurements can be obtained in grid patterns.

While throughout the specification and claims reference is made to a structure contained in the electrolyte, it should be understood that the electrolyte may comprise earth or concrete and the structure may comprise reinforced steel forming a matrix structure buried in the concrete electrolyte or may comprise a pipeline or other similar structure buried in the earth.

Throughout the specification and claims reference is made to the wheel electrode having a chamber for containing electrolytic solution. It should be understood that the use the word "containing" means that while the solution is held in the chamber there can still be leakage of the solution through the porous rim means.

It is also envisaged that the present invention may relate to a device for making an electrical survey of a structure contained in electrolyte having at least one wheel electrode as described hereinabove rotatably mounted thereto.

For a better understanding of the nature and objects of the present invention, reference may be had by way of example to the accompanying diagrammatic drawings in which.

Figure 1:
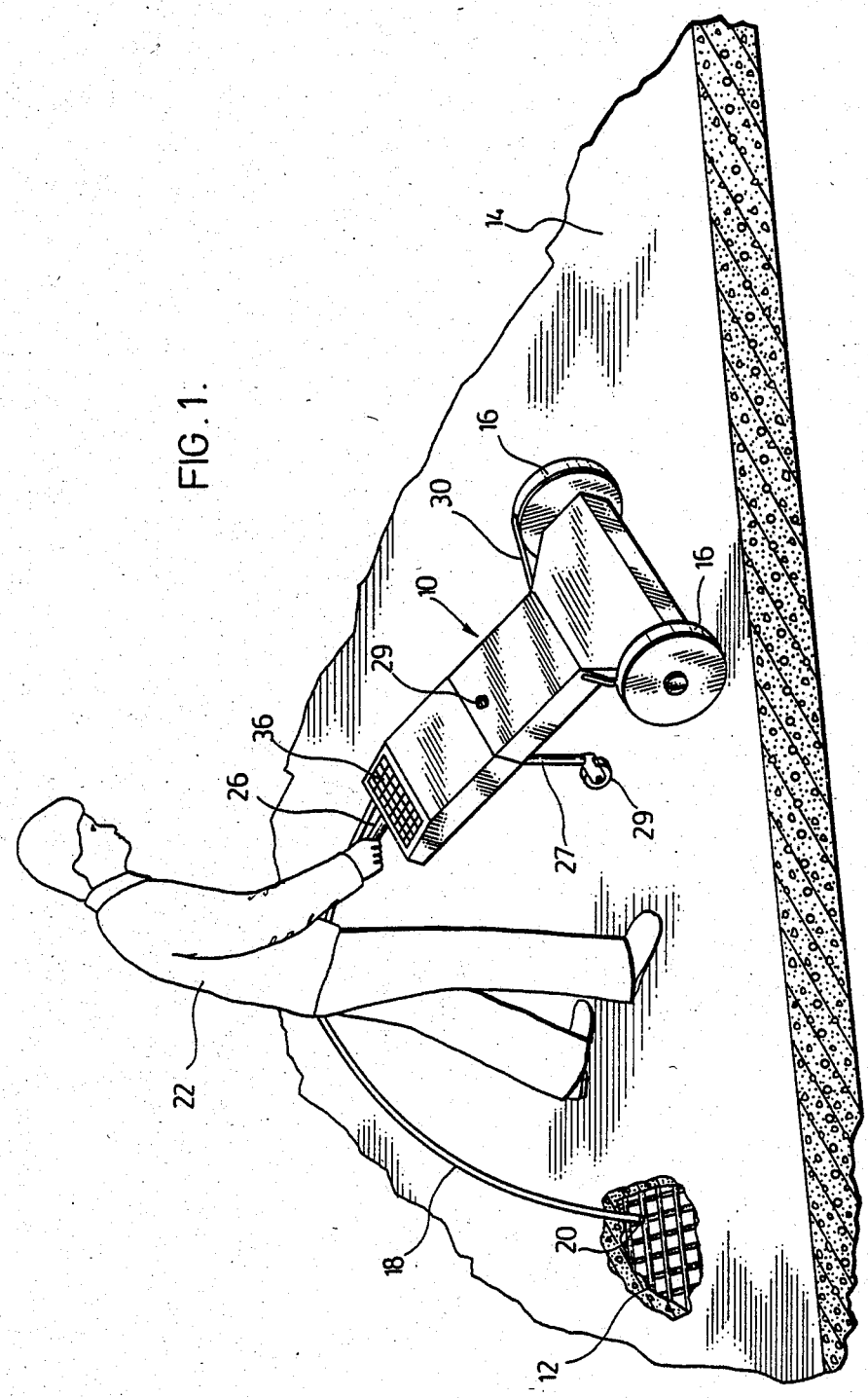
FIGS. 1, 2 and 3 illustrate various devices for making an electrical survey of a structure contained in electrolyte wherein each device includes at least one wheel electrode in accordance with the present invention.
Figure 2:
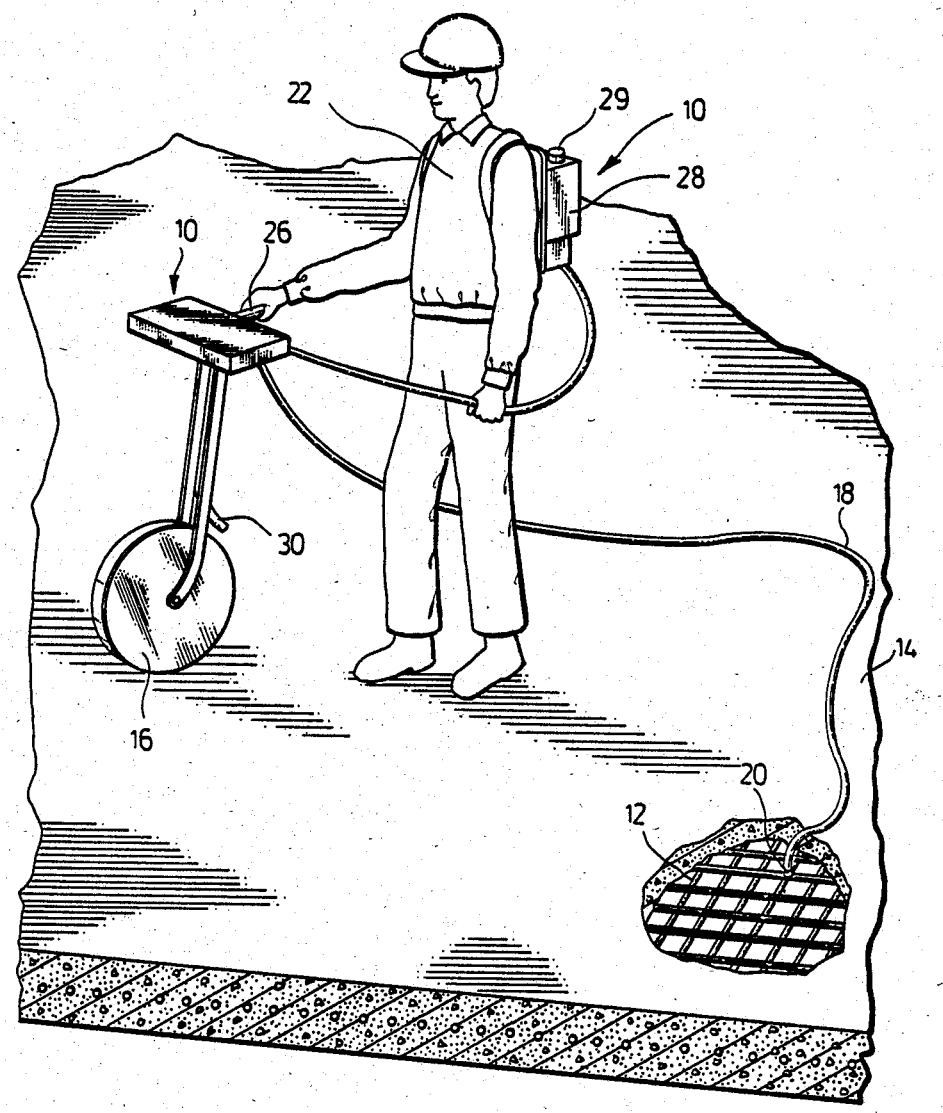
Figure 3:
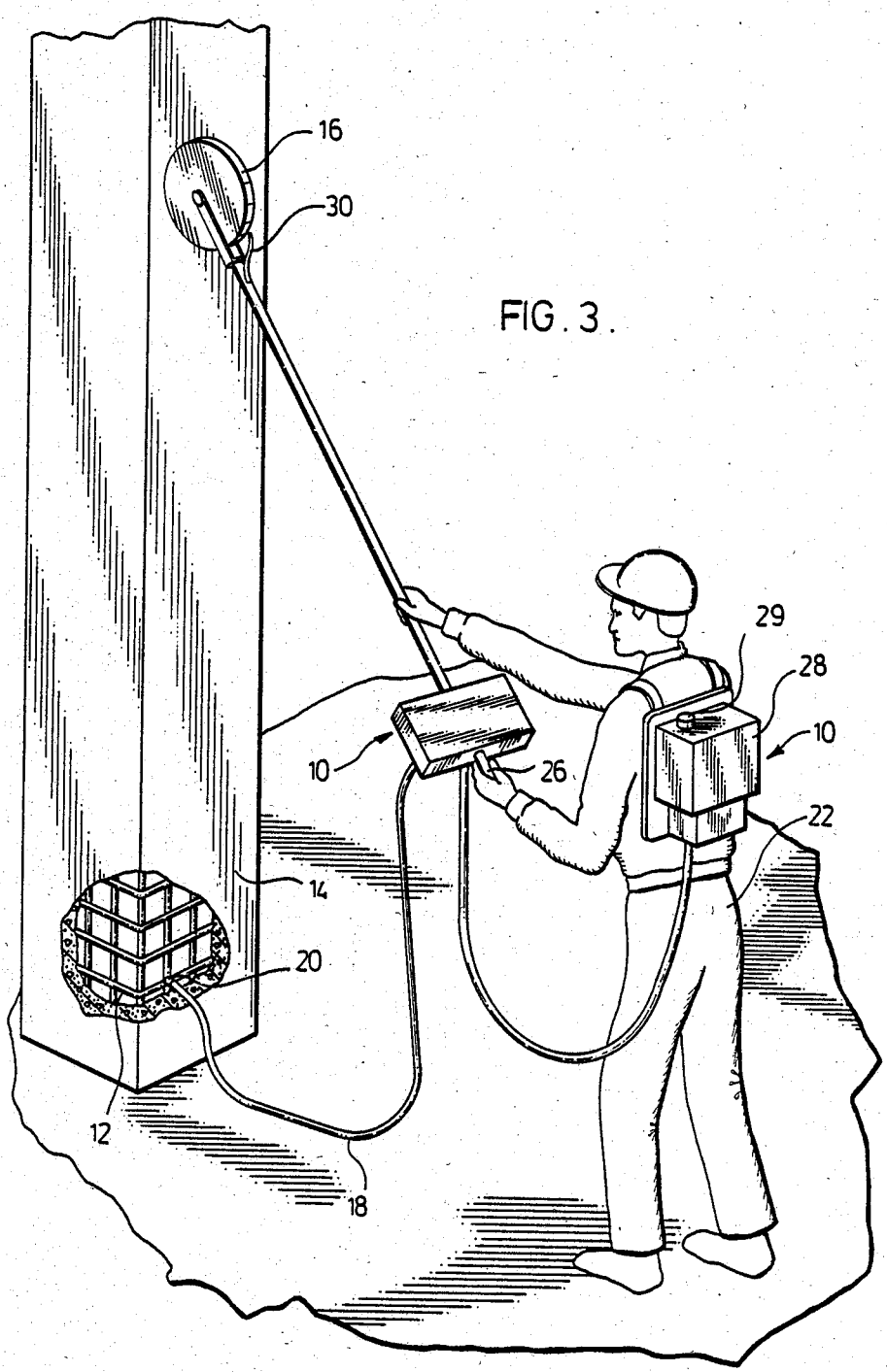

Referring now to FIGS. 1 through 3, there is shown a surveying device 10 which is used for making an electrical survey of a reinforced steel structure 12 contained in a concrete electrolyte 14. In FIG. 1 the device is shown utilising two wheel electrodes 16. In FIGS. 2 and 3 only one wheel electrode is shown.

In each of FIGS. 1 through 3 a wire or elongate conductor 18 is mechanically and electrically connected to the reinforced steel structure 12 at 20.

An operator 22 is shown using the device 10 to make an electrical survey of concrete structure 12. This survey may be made along predetermined grid lines previously established on the structure or established by the operator as he uses the device 10. In FIG. 1, all the components of the device are self-contained whereas in FIGS. 2 and 3 some of the components are carried on a backpack by the operator. While FIGS. 1 and 2 relate to surveying a concrete floor, FIG. 3 indicates that the wheel electrode can be used to survey columns.

It should be understood that the surveying device of the present invention is particularly adapted to the surveying of reinforced concrete structures such as parking garages, decks, bridges, and silos. It should be understood, however, that the surveying device of the present invention may be used in the measurement of earth potentials.

Figure 6:
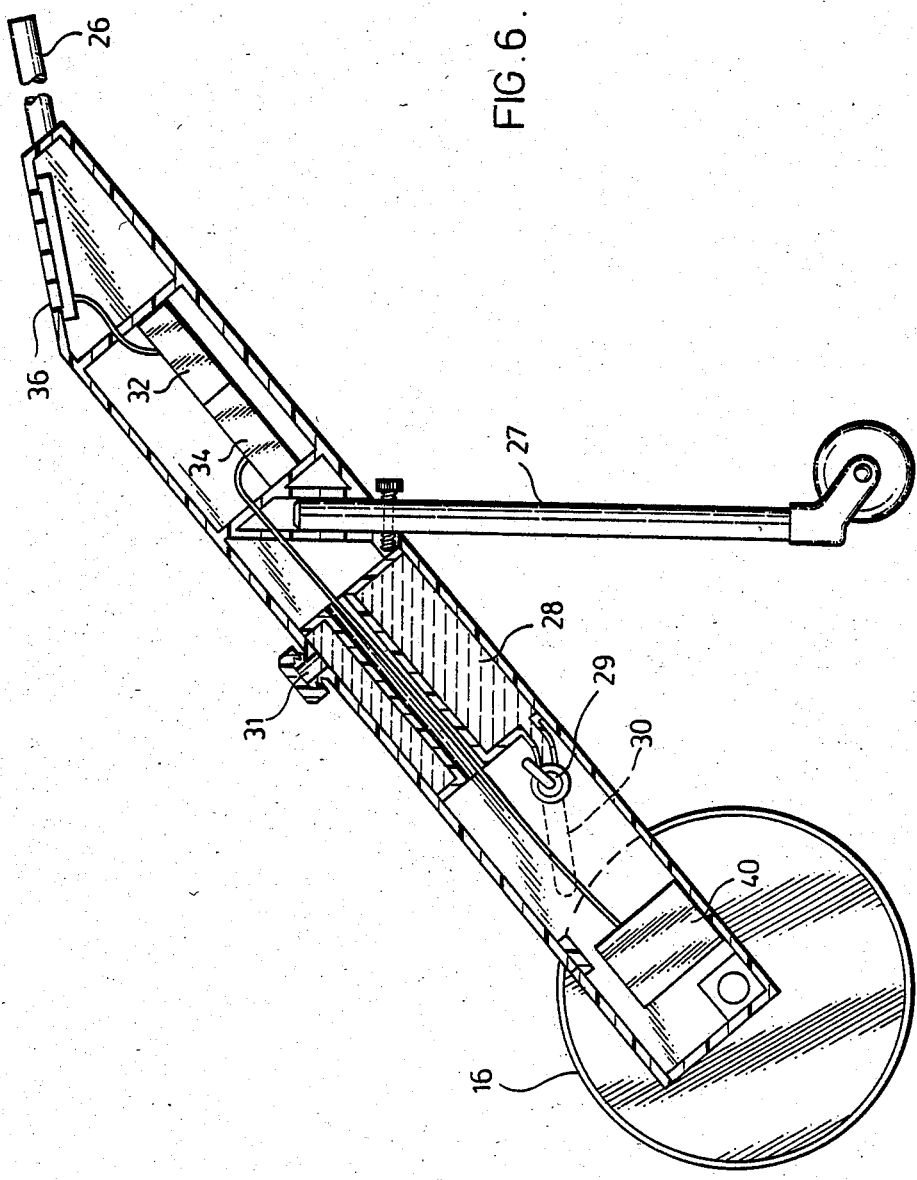
FIG. 6 is a sectional view showing the detail of the surveying device shown in FIG. 1.

Referring now to FIGS. 1 and 6 the components of the surveying device 10 are now described. The surveying device 10 includes a handle 26 which the operator 22 may hold to control the movement of the device 10 and a support arm 27 with caster 29 for supporting the weight of device 10. The surveying device 10 includes a fluid reservoir 28 and tubing passing from the reservoir to outlet 30 above the wheel electrodes 16. Water reservoir 28 can be filled through opening 31. During the operation of the surveying device 10, water is continuously fed to the wheel electrode at a controlled rate to ensure good electrical contact between the wheel electrode and electrolytic being surveyed. The surveying device 10 may include a microprocessing unit 32, a magnetic or punch tape data storage 34 and a keyboard 36 for resetting and controlling the operation of the microprocessor 32. The microprocessor 32 is electrically connected with a sensing means 72 (see FIG. 4) which provides a series of pulses to the microprocessor 72. The microprocessor 32 counts the pulses and at a predetermined count instructs the magnetic storage to read the electrolytic voltage potential sensed by the wheel electrode. The device 10 further includes a battery 40 which provides power for the electrical equipment.

The surveying devices shown in FIGS. 2 and 3 contain similar equipment to the device shown in FIGS. 1 and 6; however, some of the equipment of FIGS. 2 and 3 may be carried on a backpack by the operator 22.

Figure 4:
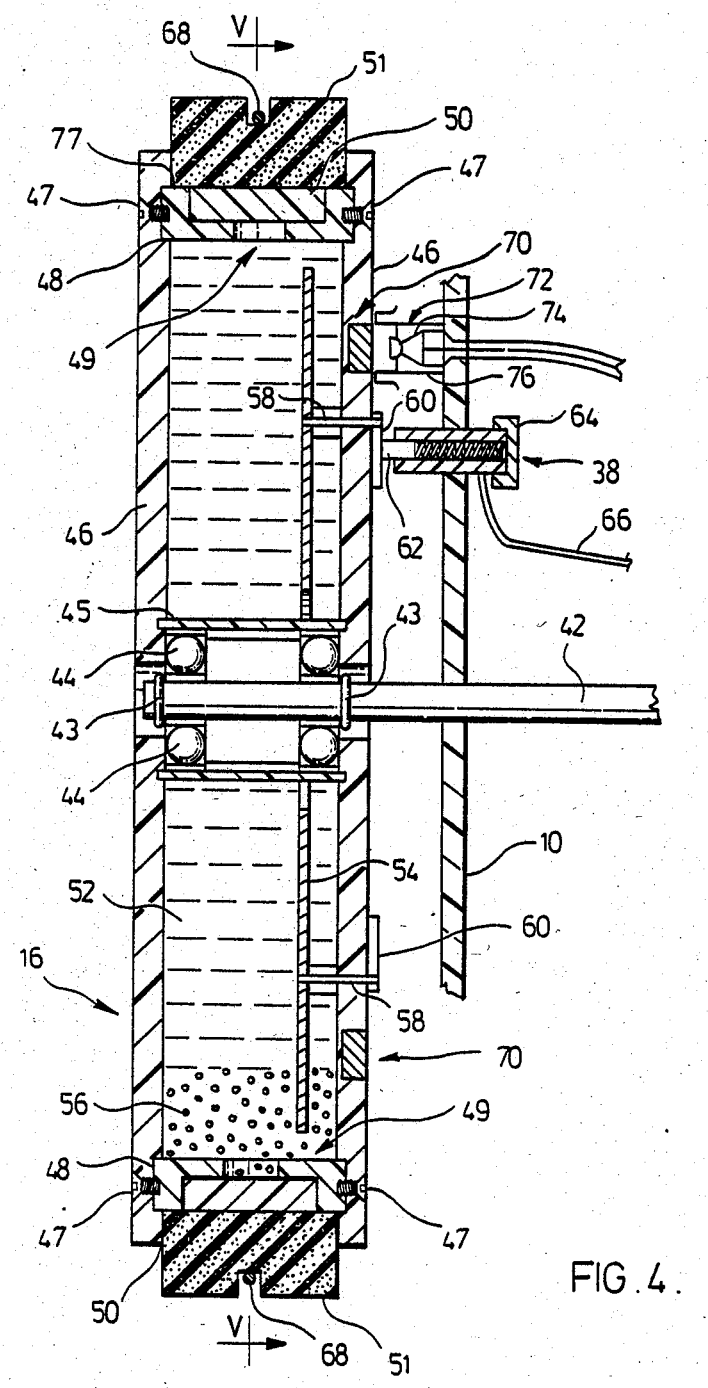
FIG. 4 is a sectional view of the wheel electrode shown rotatably mounted to the surveying device.
Figure 5:
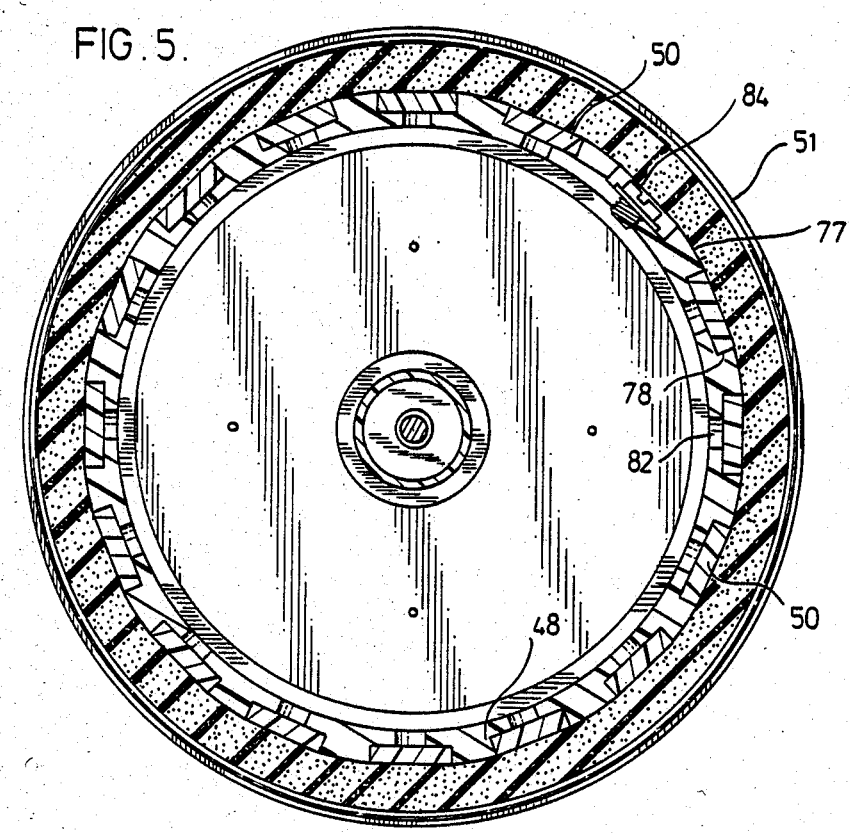
FIG. 5 is a sectional view of the wheel electrode taken at lines V—V shown in FIG. 4.

Referring now to FIGS. 4 and 5 the wheel electrode 16 of the present invention and its use in conjunction with the surveying device 10 of the present invention are now described.

Wheel electrode 16 is connected to device 10 via a shaft 42. Bearings 44 interconnect shaft 42 with a pair of spaced apart, plastic, dielectric disk means 46. The bearings 44 are held on shaft 42 by retainer clips 43. At the periphery of disks 46 there is secured by screws 47 a porous rim means 49 comprising a dielectric rim structure 48 and porous members 50. Bearings 44 are contained in bearing housing 45.

The spaced apart disks 46 define a chamber 52 within which a metal electrode 54 is carried. An electrolytic solution is carried within the chamber 52 and is shown at 56. As shown in the preferred embodiment of the wheel electrode 16, the metal electrode 54 is secured to one of the disks 46 by copper mounting pins 58. Four copper mounting pins are evenly spaced about the wheel to support the metal electrode. As shown in FIG. 4, the metal electrode 54 comprises a disc shaped structure. While in the preferred embodiment, the electrode comprises a copper-copper-sulfate electrode and the electrolytic solution is copper-copper-sulfate electrolytic solution, it should be understood that the metal electrode or electrolytic solution may be of molybdenum-molybdenum-trioxide, or silver-silver-chloride or other suitable compositions.

Also carried by the one disc 46 is a slip ring 60 of silverplated material shown at 60. Slip ring 60 electrically contacts a brush means 62 of carbon or silver. The brush means 62 is mounted with respect to the surveying device 10 by means of brush holder 64. Conductor 66 electrically interconnects brush 64 with the magnetic storage tape 34 via a voltmeter or like converting instrument.

In accordance with one aspect of the present invention the rim cover means 51 is provided to compensate for any irregularities in the reinforced concrete structure such that contact with the structure is maintained. Further, cover means 51 carries a solution supplied from the fluid reservoir of the surveying device and transfers this solution to the electrolyte. The electrically conductive solution may comprise a combination of water and electrolytes.

The cover means 51 comprises a sponge. Sponge 51 is secured to the rim structure 48 by means of an elastic band 68. The sponge rim cover means or tire 51 may comprise an elongated strip wrapped over itself and then secured by elastic band 68 or a ring of material secured by elastic band 68. When wetted the sponge rim cover 51 makes good electrical contact with the electrolyte and acts to transmit some of the conductive solution to the electrolyte. The sponge 51 is readily replaceable.

In accordance with another aspect of the present invention the wheel electrode includes signal-actuating means 70 spaced about the wheel electrode 16 at predetermined intervals for causing a series of electrical signals to be produced as the wheel electrode rotates. The count of the signals by the microprocessor unit is indicative of the distance travelled by the wheel electrode 16 over the electrolyte. The device 10 includes signal-producing means 72 which are responsive to the passage of the signal-actuating means 70 past the signal-actuating means so as to generate the electrical signals.

As shown in FIG. 4, the signal-actuating means comprise a plurality of permanent magnets mounted by epoxy bonding or the like on the outside portion of the one dielectric disk 46. The permanent magnets are spaced about the disk and follow an annular path (See FIG. 7) which is concentric with the axis of rotation of the disk about shaft 42. The signal-producing means 72 comprises a Hall effect transistor 74 which turns on for a predetermined time to generate a pulse as a magnet passes the Hall effect transistor 74. A transistor holding means 76 is provided in the device 10 to hold the Hall effect transistor 74 on the device 10. The transistor 74 is located adjacent the annular path of travel of the magnets and generates an electrical signal each time a magnet passes the transistor. The microprocessor takes a reading of sensed electrolytic voltage and converts it to a binary format for storage in the storage means 34 along with the coordinates of the measurement after the wheel electrode has travelled a predetermined distance. In the event that two wheel electrodes are being used, the microprocessor may work in such a fashion as to accept information in parallel.

In accordance with another aspect of the present invention the rim structure 48 of the wheel electrode 16 comprises a series of "ionic windows". These windows are provided by spacing about the outer axial surface 77 of the rim structure a series of recesses 78. Inside each recess 78 there is provided a porous member 50 having a predetermined rate of permeation and securable by bonding epoxy or like material in the recess 78. The porous members 50 may comprise a ceramic material which is preferably a sintered aluminum oxide. The sintered aluminum oxide becomes saturated with the electrolytic solution as electrolytic solution passes through apertures 82 positioned in the rim structure 48 beneath each recess 78. Electrolytic solution passes from the chamber 52 through the apertures 82 permeates the sintered aluminum oxide disk 50 and provides a conductive path to the wet sponge 51 on the outside of the wheel electrode 16.

A plug 84 is shown in one of the recesses 78. The plug 84 is removable to facilitate the introduction of electrolytic solution into the chamber 52. It should be understood that the spacing between the recesses 78 is such to allow a conductive path at all times between the electrolyte being surveyed and the metal electrode 54 within the wheel electrode 16.

Figure 7:
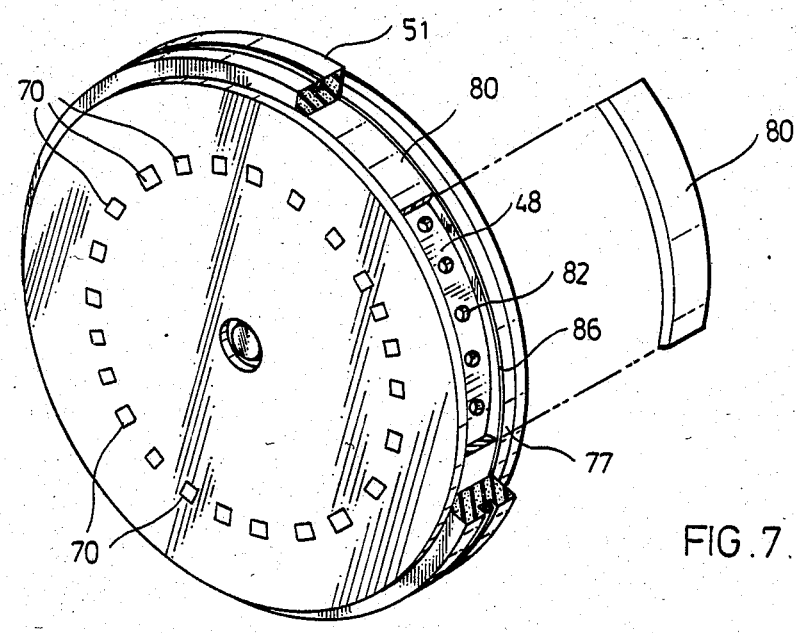
FIG. 7 is a perspective view of an alternative embodiment for the rim structure of the present invention.

Referring to FIG. 7 an alternate embodiment for the ionic window is shown. In this embodiment, instead of having a series of recesses, a continuous groove 86 is provided. The porous members may comprise a single or series of segments of aluminum oxide 80. Along the bottom of the groove there is provided a plurality of apertures allowing the sintered oxide to be in contact with the electrolytic solution at all times and provide a conductive path between the metal electrode and the electrolyte to be surveyed.

The embodiments of the invention in which an exclusive property or privilege is claimed are defined as follows:

1. A wheel electrode for use with a device for making electrical surveys of structures contained in electrolyte, said wheel electrode comprising:

porous rim means including a dielectric rim structure having at least one recess in its axial surface and a plurality of apertures passing through the rim structure into the recess, and at least one porous member securable in said recess and having a predetermined rate of permeation whereby electrolyte solution provides a continuous conducting path through said porous members;

a chamber for containing the electrolytic solution which communicates with said porous rim means; and metal electrode means in said chamber in contact with the electrolytic solution for sensing electrolytic voltage potentials in said electrolyte.

2. A wheel electrode as defined in claim 1 including a plurality of recesses spaced apart at predetermined intervals, at least one of said apertures being located below each of said recesses, and one of said porous members being located in each of said recesses.

3. A wheel electrode as defined in claim 2 wherein said predetermined intervals are chosen to maintain conduction from said electrolyte to said metal electrode means as said wheel rotates on said electrolyte.

4. A wheel electrode as defined in claim 1 wherein said porous members comprise a ceramic material.

5. A wheel electrode as defined in claim 1 wherein said porous members comprise a sintered aluminum oxide.

6. A wheel electrode according to claim 2 wherein said recesses are disc shaped, and each said porous rim means comprises a disc shaped sintered aluminum oxide material.

7. A wheel electrode according to claim 3 wherein plug means is removably securable in one of said recesses to allow said chamber to be filled with the electrolytic solution.

8. A wheel electrode according to claim 1 further including elastic porous rim cover means securable about said rim means for contacting said electrolyte, said rim cover means being adapted to carry an electrically conductive solution to said electrolyte as said rim cover means makes contact with said electrolyte.

* * * * *